US009682113B2

(12) United States Patent
Jung et al.

(10) Patent No.: US 9,682,113 B2
(45) Date of Patent: Jun. 20, 2017

(54) **METHOD FOR PREVENTING, IMPROVING OR TREATING CORNEA DAMAGES USING EXTRACTS OF *DIOSPYROS KAKI***

(71) Applicant: Korea Institute of Science and Technology, Seoul (KR)

(72) Inventors: Sang Hoon Jung, Gangneung-si (KR); Kyung A Kim, Gangneung-si (KR); Suk-Woo Kang, Gangneung-si (KR); Joo Young Lee, Gangneung-si (KR); Hong Ryul Ahn, Gangneung-si (KR); Youngwoo Song, Gangneung-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/132,899

(22) Filed: Apr. 19, 2016

(65) Prior Publication Data

US 2016/0310551 A1   Oct. 27, 2016

(30) Foreign Application Priority Data

Apr. 21, 2015   (KR) .................. 10-2015-0055608

(51) Int. Cl.

| | | |
|---|---|---|
| *A61K 36/44* | (2006.01) | |
| *A61K 9/00* | (2006.01) | |
| *A23L 1/30* | (2006.01) | |
| *A23L 33/105* | (2016.01) | |

(52) U.S. Cl.
CPC ............ *A61K 36/44* (2013.01); *A23L 1/3002* (2013.01); *A23L 33/105* (2016.08); *A61K 9/0053* (2013.01)

(58) Field of Classification Search
CPC .................................................... A61K 36/44
USPC ........................................................ 424/777
See application file for complete search history.

(56) References Cited

U.S. PATENT DOCUMENTS

2010/0247434 A1   9/2010   Greenway et al.

FOREIGN PATENT DOCUMENTS

| | | | |
|---|---|---|---|
| KR | 2000-0039833 A | 7/2000 | |
| KR | 2002-0084875 A | 11/2002 | |
| KR | 10-0955389 B1 | 4/2010 | |
| KR | 10-2010-0054653 A | 5/2010 | |
| KR | 10-2011-0082689 A | 7/2011 | |
| KR | 10-2011-0117876 A | 10/2011 | |
| KR | 10-2012-0031695 A | 4/2012 | |
| KR | 10-2013-0033623 A | 4/2013 | |
| KR | 10-1286133 B1 | 7/2013 | |
| KR | 10-2013-0133338 A | 12/2013 | |
| KR | 20130133338 A | * 12/2013 | |
| KR | 10-2014-0063559 A | 5/2014 | |
| KR | 10-1396438 B1 | 5/2014 | |
| KR | 10-1395875 B1 | 6/2014 | |

OTHER PUBLICATIONS

Hollyfield et al. "Oxidative damage-induced inflammation initiates age-related macular degeneration", Nature Medicine, vol. 14, No. 2, Feb. 2008.*
Ouyang, Ping, et al., "Effects of flavone from leaves of *Diospyros kaki* on adventitial fibroblast proliferation induced by advanced glycation end-points in vitro" Academic Journal of the First Medical College of PLA, (2003): 1260-1262.
Bei, Weijian, et al. "Flavonoids from the leaves of *Diospyros kaki* reduce hydrogen peroxide-induced injury of NG108-15 cells." Life Sciences 76.17 (2005): 1975-1988.
Ouyang, Ping, et al., "Effects of Flavone from Leaves of *Diospyros kaki* on Expression of Apoptosis Signal-Regulating Kinase 1 and Rat Vascular Smooth Muscle Cells Proliferation by Tumor Necrosis Factor α in Vitro." Journal of Chinese Medicinal Materials (2007): 819-822.
Bei, Weijian, et al. "Neuroprotective effects of a standardized flavonoid extract from *Diospyros kaki* leaves." Journal of Ethnopharmacology 126.1 (2009): 134-142.
Kim, Seung Hyun, et al. "Effects and action mechanism of *Diospyros kaki* on the differentiation of human leukemia HL-60 cells." Oncology Reports 23.1 (2010): 89-95.
Khanal, Prem, et al. "24-Hydroxyursolic Acid from the Leaves of the *Diospyros Kaki* (Persimmon) Induces Apoptosis by Activation of AMP-Activated Protein Kinase." Planta Medica 76.7 (2010): 689-693.
Ohguchi, Kenji, et al. "Inhibitory Effects of Flavonoid Glycosides Isolated from the Peel of Japanese Persimmon (*Diospyros kaki* 'Fuyu') on Melanin Biosynthesis." Biological and Pharmaceutical Bulletin 33.1 (2010): 122-124.
Kawakami, Kayoko, et al. "Major Water-Soluble Polyphenols, Proanthocyanidins, in Leaves of Persimmon (*Diospyros kaki*) and Their α-Amylase Inhibitory Activity." Bioscience, Biotechnology, and Biochemistry 74.7 (2010): 1380-1385.
Li, Wanwen, et al. "Self-nanoemulsifying drug delivery system of persimmon leaf extract: Optimization and bioavailability studies." International Journal of Pharmaceutics 420.1 (2011): 161-171.
Matsumoto, Kenji, et al. "Induction of uncoupling protein-1 and -3 in brown adipose tissue by kaki-tannin in type 2 diabetic NSY/Hos mice." Food and Chemical Toxicology 50.2 (2012): 184-190.
Celep, Engin, et al. "A comparative study on the in vitro antioxidant potentials of three edible fruits: Cornelian cherry, Japanese persimmon and cherry laurel." Food and Chemical Toxicology 50.9 (2012): 3329-3335.
Kim, Hui-Hun, et al. "Inhibitory effects of *Diospyros kaki* in a model of allergic inflammation: Role of cAMP, calcium and nuclear factor-kB." International Journal of Molecular Medicine 32.4 (2013): 945-951.
Sun, Lijun, et al. "Flavonoids from persimmon (*Diospyros kaki*) leaves (FPL) attenuate $H_2O_2$-induced apoptosis in MC3T3-E1 cells via the NF-kB pathway." Food & Function 5.3 (2014): 471-479.

(Continued)

*Primary Examiner* — Chris R Tate
*Assistant Examiner* — Deborah Davis
(74) *Attorney, Agent, or Firm* — NSIP Law (57) ABSTRACT

Disclosed is a method for preventing, improving and/or treating cornea damage or a corneal disease, including administering an effective amount of an extract of a persimmon tree for preventing, improving or treating cornea damage to a subject in need thereof. The extract may be a persimmon leaf extract and the extract is effective in suppressing inflammation of the cornea and protecting corneal cells.

14 Claims, 4 Drawing Sheets

(56) References Cited

OTHER PUBLICATIONS

Zhang, Sheng-hai, et al. "Studies of the microbial metabolism of flavonoids extracted from the leaves of *Diospyros kaki* by intestinal bacteria." Archives of Pharmacal Research 38.5 (2015): 614-619.
Chang, Jin-Hong, et al. "Corneal neovascularization." *Current opinion in ophthalmology* 12.4 (2001): 242-249. (8 pages, in English).
Kim, Gyeongsu. *Anti-Inflammatory Effects of Diospyros kaki Thunb. Leaves and Its Components by Inhibition of NF-KB Pathway Against LPS-Induced Toxicity in Macrophages.* Thesis. Wonkwang University, 2014. (106 pages, in English).

* cited by examiner

METHOD FOR PREVENTING, IMPROVING OR TREATING CORNEA DAMAGES USING EXTRACTS OF *DIOSPYROS KAKI*

CROSS-REFERENCE TO RELATED APPLICATION

This application claims the priority of Korean Patent Application No. 10-2015-0055608, filed on Apr. 21, 2015, and all the benefits accruing therefrom under 35 U.S.C. §119, the contents of which in its entirety are herein incorporated by reference.

BACKGROUND

1. Field

The present disclosure discloses a method for preventing, improving and/or treating cornea damage or a corneal disease, including administering an effective amount of an extract of a persimmon tree for preventing, improving and/or treating the cornea damage or corneal disease to a subject in need thereof.

2. Description of the Related Art

Keratitis refers to a condition in which the eye's cornea is damaged and becomes inflamed due to edema. The symptoms of keratitis include impaired eyesight, pain, red eye, tearing, dazzling, increased tears, foreign body sensation, etc. and severe inflammation may lead to the destruction of the whole cornea and significantly affect vision.

Keratitis can be largely classified into infective and non-infective keratitis. Specifically, infective keratitis is caused by various pathogens such as bacteria, viruses, fungi, etc. And, non-infective keratitis can be subdivided, for example, into exposure keratitis caused by prolonged exposure of the cornea to external air, toxic keratitis caused by drugs, neurotrophic keratitis caused by corneal nerve damage, contact lens acute red eye, physical trauma, etc.

Persimmon (*Diospyros kaki*) is a fruit tree that grows in East Asia, including Korea, China, Japan, etc. The tree is 6-14 m tall. The outer bark is cleaved like scales and the small branches have brown hair. The leaves, which grow in alternation, are coriaceous and elliptic-ovate. The leaves are 7-17 cm long and 4-10 cm wide and are not toothed. The petiole is 5-13 mm long and hairy. The yellow-white flowers, bisexual or unisexual, bloom at the axils in May to June. The male flower has 16 stamens but the bisexual flower has 4-16 stamens. The female flower is 15-18 mm long. The style is hairy and split lengthwise and the ovary has 8 locules. The fruit is oval or oblong and ripens yellow to red-orange in October.

In traditional medicine, the fruit of persimmon has been used to relieve heat from the heart or lungs due to its cold properties. Likewise, the leaf of persimmon also has cold and bitter properties. According to Dongui Bogam and Boncho Gangmok, the persimmon leaf is effective in chronic diseases such as cardiovascular diseases, diabetes, peptic ulcer, etc. Also, the persimmon leaf is known to be rich in water-soluble vitamins such as vitamins A, C, P, etc. as well as tannins and catechins and, thus, may be helpful in improving immunity and maintaining the homeostasis of the body. However, nothing is known about the effect of inhibiting cornea damage and protecting corneal cells of a persimmon extract.

SUMMARY

In an aspect, the present disclosure is directed to providing a method for preventing, improving and/or treating cornea damage or a corneal disease by administering an effective amount of an extract of a persimmon tree for preventing, improving and/or treating the cornea damage or corneal disease to a subject in need thereof.

In an aspect, the present disclosure provides a method for preventing, improving or treating cornea damage, including administering an effective amount of an extract of a persimmon tree for preventing, improving or treating cornea damage to a subject in need thereof.

In an exemplary embodiment, the extract may be administered in the form of a pharmaceutical composition.

In an exemplary embodiment, the extract may be administered in the form of a health food composition.

In an exemplary embodiment, the persimmon tree may be *Diospyros kaki*.

In an exemplary embodiment, the extract may be a leaf extract of the persimmon tree.

In an exemplary embodiment, the extract may be a $C_1$-$C_6$ alcohol extract.

In an exemplary embodiment, the cornea damage may be caused by a corneal disease or cause a corneal disease.

In an exemplary embodiment, the cornea damage may be one or more selected from a group consisting of keratitis, corneal ulcer and corneal abrasion.

In an exemplary embodiment, the extract may inhibit the expression of inflammatory cytokines.

In an exemplary embodiment, the inflammatory cytokine may be one or more selected from a group consisting of IL-1α, IL-1β, TNF-α, MCP-1 (monocyte chemoattractant protein-1) and IL-6.

In an exemplary embodiment, the extract may inhibit the damage of the corneal stromal layer.

In an exemplary embodiment, the extract may promote the proliferation of corneal epithelial cells.

In an aspect, the present disclosure provides a method for preventing, improving and/or treating cornea damage or a corneal disease by administering an effective amount of an extract of a persimmon tree for preventing, improving and/or treating the cornea damage or corneal disease to a subject in need thereof.

DETAILED DESCRIPTION

Hereinafter, the present disclosure is described in detail.

In an aspect, the present disclosure provides a method for preventing, improving and/or treating cornea damage and/or a corneal disease by administering an effective amount of an extract of a persimmon tree for preventing, improving and/or treating the cornea damage and/or corneal disease to a subject in need thereof.

In an exemplary embodiment, the extract may be administered in the form of a pharmaceutical composition. The pharmaceutical composition contains the extract of a persimmon tree as an active ingredient.

In an exemplary embodiment, the extract may be administered in the form of a health food composition. The health food composition contains the extract of a persimmon tree as an active ingredient.

In the present disclosure, the "active ingredient" refers to an ingredient which exhibits a desired activity when used alone or together with a carrier, etc. which is inactive in itself.

In the present disclosure, the "corneal disease" refers to any disease caused by cornea damage.

In the present disclosure, the "cornea damage" refers to damage to the cornea caused by, e.g., pathogens, inflammation, physical irritation (e.g., contact lens or UV), chemical irritation (e.g., drug), nerve damage, accumulated fatigue, etc., although not being limited thereto. It may be accompanied by such symptoms as pain, red eye, corneal opacity, dazzling, foreign body sensation, etc.

In an exemplary embodiment, the composition may contain 0.1-50 wt % of the extract of a persimmon tree based on the total weight of the composition. By containing 0.1-50 wt % of the extract of a persimmon tree based on the total weight of the composition, the composition exhibits significant effect of preventing, improving and/or treating the cornea damage and/or corneal disease and provides superior effect in terms of efficiency and economy. Specifically, the composition may contain 0.5-45 wt %, 0.5-40 wt %, 0.5-35 wt %, 0.5-30 wt %, 0.5-25 wt %, 0.5-20 wt %, 1.0-15 wt % or 1.0-10 wt % of the extract of a persimmon tree based on the total weight of the composition.

In an exemplary embodiment, the persimmon tree may be *Diospyros kaki*.

In an exemplary embodiment, the extract may be an extract of one or more selected from a group consisting of the root, stem, leaf, flower and branch of persimmon. Specifically, the extract may be a leaf extract of the persimmon tree.

In the present disclosure, the extract not only includes a crude extract but also a processed extract obtained by further processing the extract, e.g., by drying, concentration, fractionation, fermentation, etc.

In the present disclosure, the extract may be an extract obtained by extracting one or more selected from a group consisting of the root, stem, leaf, flower and branch of persimmon or a powder thereof. The extraction may be performed by a method commonly used in the related art.

In an exemplary embodiment, the extract may be prepared by a method including the following steps, although not being limited thereto:

1) a step of extracting dried persimmon leaf (*Diospyros kaki*) by adding an extraction solvent;

2) a step of filtering the extract of the step 1); and 3) a step of concentrating the extract of the step 2) under reduced pressure.

The method for preparing the extract of a persimmon tree may further include 4) a step of preparing fractions by further extracting the extract of the step 3) with an organic solvent.

The persimmon leaf in the step 1) may be either cultivated one or commercially available one without limitation.

The extraction solvent in the step 1) may be water, an alcohol or a mixture thereof, specifically a $C_1$-$C_6$ or $C_1$-$C_4$ lower alcohol or a mixture thereof, more specifically an aqueous solution of methanol or ethanol, although not being limited thereto. The amount of the extraction solvent may be specifically 1-20 times, more specifically 10 times, based on the weight of the persimmon leaf, although not being limited thereto.

In the step 1), the extraction may be performed by hot water extraction, immersion extraction, reflux condensation extraction, ultrasonic extraction, etc. Specifically, ultrasonic extraction may be performed 1-5 times. The extraction may be performed specifically at 10-100° C., more specifically at room temperature, although not being limited thereto. The extraction may be performed specifically for 1 hour to 7 days, more specifically for 3-7 days, although not being limited thereto.

The extraction may also be performed by supercritical extraction, subcritical extraction, high-temperature extraction, high-pressure extraction, extraction using an adsorbent resin such as XAD or HP-20, microbial fermentation, natural fermentation, etc. Specifically, the extraction may be performed under reflux at elevated temperatures or room temperature, although not being limited thereto. The extraction may be performed specifically 1-5 times, more specifically 3 times, although not being limited thereto.

In an exemplary embodiment, the leaf extract may be prepared by supercritical fluid extraction using carbon dioxide under reduced pressure at high temperature. In general, a supercritical fluid has the properties of liquid and gas at the same time at a temperature and pressure above its critical point and chemically has a polarity similar to that of a nonpolar solvent. Due to these characteristics, the supercritical fluid is used to extract oil-soluble substances. Carbon dioxide becomes a supercritical fluid having the properties of liquid and gas at the same time as it passes the critical point and, as a result, its solubility for oil-soluble solutes is increased. As the supercritical carbon dioxide passes an extraction container containing a given amount of sample, the oil-soluble substances contained in the sample are extracted to the supercritical carbon dioxide. After the oil-soluble substances have been extracted, supercritical carbon dioxide containing a small amount of cosolvent may be flown to the sample remaining in the extraction container to extract the ingredients that have not been extracted with the pure supercritical carbon dioxide. The cosolvent may be one or more selected from a group consisting of chloroform, ethanol, methanol, water, ethyl acetate, hexane and diethyl ether. The carbon dioxide contained in the extracted sample is evaporated into the air at room temperature and the cosolvent may be removed using a vacuum evaporator.

In an exemplary embodiment, the leaf extract may be prepared by ultrasonic extraction using the energy generated by ultrasonic vibration. Local heating of the solvent occurring as the insoluble substances contained in a sample may be destroyed in an aqueous solvent by ultrasound increases the kinetic energy of reactant particles sufficiently for reaction. Also, high pressure generated by the ultrasonic impact increases extraction efficiency by facilitating the mixing of the substances contained in the sample with the solvent.

In an exemplary embodiment, the leaf extract may be prepared by fermentation. After crushing persimmon leaf finely to about 100-500 mesh, 1-50 g/L of a commonly used microbiological culture medium is added and then 10,000-100,000 CFU/L of microorganisms such as yeast, *E. coli*, etc. are added. After culturing the microorganisms at 30-37° C. under a common microbiological culture condition, under aerobic or anaerobic condition of pH 5-7, for about 5-10 days, the extract may be obtained through aging and filtering.

Specifically, the concentration under reduced pressure in the step 3) may be performed using a vacuum rotary evaporator, although not being limited thereto. The extract may be dried after the concentration under reduced pressure. Specifically, the drying may be performed by low-pressure drying, vacuum drying, boiling drying, spray drying, room-temperature drying or freeze-drying, although not being limited thereto.

Specifically, the organic solvent in the step 4) may be n-hexane, methylene chloride, ethyl acetate or n-butanol, although not being limited thereto.

Specifically, the fraction in the step 4) may be one of a n-hexane fraction, a methylene chloride fraction, an ethyl acetate fraction, a n-butanol fraction and a water fraction obtained by suspending the leaf extract of the persimmon tree in water and then sequentially and systematically fractionating with n-hexane, methylene chloride, ethyl acetate, n-butanol and water. More specifically, it may be a methylene chloride fraction, although not being limited thereto. The fraction may be obtained by fractionating leaf extract 1-5 times, specifically 3 times. Specifically, concentration may be performed under reduced pressure after the fractionation, although not being limited thereto.

In an exemplary embodiment of the present disclosure, the extract may be obtained by crushing persimmon leaf to a suitable size and adding to an extraction container, adding an aqueous ethanol solution and keeping at room temperature, filtering with filter paper and then concentrating and freeze-drying the filtrate. In addition, fractions of the extract of a persimmon tree may be obtained by sequentially and systematically fractionating the obtained extract of a persimmon tree with n-hexane, methylene chloride, ethyl acetate, n-butanol and water using a separatory funnel.

The pharmaceutical composition and the health food composition containing the extract of a persimmon tree according to the present disclosure are effective in preventing, improving and/or treating cornea damage and/or a corneal disease by protecting the cornea by inhibiting the damage of corneal cells and corneal layers and suppressing the inflammatory response of the corneal cells.

In an exemplary embodiment, the corneal disease may be one or more selected from a group consisting of keratitis, corneal ulcer and corneal abrasion.

In an exemplary embodiment, the cornea damage may be caused by one or more selected from a group consisting of keratitis, corneal ulcer and corneal abrasion.

In an exemplary embodiment, the pharmaceutical composition and the health food composition may protect corneal cells and suppress the inflammatory response of the corneal cells.

In an exemplary embodiment, the pharmaceutical composition and the health food composition may inhibit the expression of inflammatory cytokines.

In an exemplary embodiment, the inflammatory cytokine may be one or more selected from a group consisting of IL-1α, IL-1β, TNF-α, MCP-1 (monocyte chemoattractant protein-1) and IL-6.

In an exemplary embodiment, the pharmaceutical composition and the health food composition may inhibit the damage of the corneal stromal layer.

In an exemplary embodiment, the pharmaceutical composition and the health food composition may promote the proliferation of corneal epithelial cells.

In another aspect, the present disclosure provides a method for preventing, improving or treating keratitis, corneal ulcer and/or corneal abrasion, including administering an effective amount of an extract of a persimmon tree for preventing, improving and/or treating keratitis, corneal ulcer and/or corneal abrasion to a subject in need thereof.

The pharmaceutical composition of the present disclosure may further contain a suitable carrier, excipient and diluent commonly used in the preparation of medicine.

The carrier, excipient and diluent that may be contained in the pharmaceutical composition of the present disclosure include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil.

The pharmaceutical composition of the present disclosure may formulated to an oral formulation such as a powder, a granule, a tablet, a capsule, a suspension, an emulsion, a syrup, an aerosol, etc., a formulation for external application, a suppository or a sterilized solution for injection according to common methods.

The formulation is prepared using a commonly used diluent or excipient such as a filler, an extender, a binder, a humectant, a disintegrant, a surfactant, etc. Solid formulations for oral administration include a tablet, a pill, a powder, a granule, a capsule, etc. These solid formulations are prepared by mixing the composition of the present disclosure with at least one excipient, e.g., starch, calcium carbonate, sucrose, lactose, gelatin, etc. In addition to the simple excipient, lubricants such as magnesium stearate and talc are also used. Liquid formulations for oral administration include a suspension, a liquid formulation for internal use, an emulsion, a syrup, etc. It may contain, in addition to a commonly used simple diluent such as water and liquid paraffin, various excipients, e.g., a humectant, a sweetener, an aromatic, a preservative, etc. Formulations for parenteral administration include a sterilized aqueous solution, a non-aqueous solution, a suspension, an emulsion, a freeze-dried formulation and a suppository. As a solvent of the non-aqueous solution or suspension, propylene glycol, polyethylene glycol, vegetable oil such as olive oil, an injectable ester such as ethyl oleate, etc. may be used. As a base of the suppository, witepsol, macrogol, Tween 61, cocoa butter, laurin butter, glycerogelatin, etc. may be used.

The pharmaceutical composition of the present disclosure may be administered orally or parenterally (e.g., intravenously, subcutaneously, intraperitoneally or topically) depending on purposes. The administration dosage may vary depending on the physical condition, body weight, age and sex of a patient, diet, rate of excretion, severity of a disease, drug type, administration time, administration method, administration route, administration period, etc. A daily administration dosage of 0.0001-500 mg/kg, specifically 0.001-100 mg/kg, based on a freeze-dried extract, may be administered once or several times a day.

The health food composition of the present disclosure may be in the form of a drink, meat, sausage, bread, biscuit, rice cake, chocolate, candy, snack, confectionery, pizza, instant noodle, other noodles, gum, dairy products including ice cream, soup, beverage, alcoholic beverage, vitamin complex, etc. The health food includes all health foods in common sense.

The leaf extract of the present disclosure may be added to food as it is or after being mixed with another food or food ingredient, according to common methods. The amount of the active ingredient may be determined adequately depending on purposes (for prevention or improvement). In general, the amount of the extract in the health food may be 0.1-90 parts by weight based on the total weight of the food. However, in case of long-term use for improving health or hygiene, the amount may be smaller than the above range. Furthermore, the amount of the active ingredient may be larger than the above range because there is no safety problem.

A health functional drink composition of the present disclosure may contain ingredients other than the extract of a persimmon tree as an essential ingredient. The additionally used ingredient is not specially limited and may include various flavors, natural carbohydrates, etc. as in common drinks. The natural carbohydrate may be, for example, a monosaccharide, e.g., glucose, fructose, etc., a disaccharide, e.g., maltose, sucrose, etc., a polysaccharide, e.g., dextrin, cyclodextrin, etc., a sugar alcohol such as xylitol, sorbitol, erythritol, etc. In addition, a natural flavor (thaumatin, stevia extract (e.g., rebaudioside A, glycyrrhizin, etc.)) or a synthetic flavor (saccharin, aspartame, etc.) may be used as the flavor. The amount of the natural carbohydrate may be generally about 1-20 g, specifically about 5-12 g, per 100 mL of the composition of the present disclosure.

In addition to the extract of a persimmon tree of the present disclosure, the composition may further contain various nutrients, vitamins, minerals (electrolytes), flavors such as synthetic flavors and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated drinks, etc. In addition, the extract of a persimmon tree of the present disclosure may contain pulp for preparing natural fruit juice, fruit juice drink and vegetable drink. These ingredients may be used independently or in combination. The amount of these additives may be generally about 0.1-20 parts by weight per 100 parts by weight of the extract of a persimmon tree of the present disclosure.

Hereinafter, the present disclosure will be described in detail through examples. However, the following examples are for illustrative purposes only and it will be apparent to those of ordinary skill in the art that the scope of the present disclosure is not limited by the examples.

EXAMPLE

Preparation of an Extract of a Persimmon Tree

After drying and crushing persimmon leaf, 7 L of industrial ethanol (conc. 95%) was added to 800 g of the dried persimmon leaf powder and ultrasonic extraction was performed for 4 hours. After filtering the extract and adding 7 L of ethanol to the residual, ultrasonic extraction was performed for 4 hours. A total of 35 L of extract was obtained by repeating this procedure 4 times. Then, 33 g of an ethanol extract ('EEDK') was obtained by concentrating 35 L of the extract under reduced pressure at 35° C.

TEST EXAMPLE 1

Animal Model of Chemically Induced Cornea Damage

Benzalkonium chloride (BAC) is widely used as a preservative in eye drops due to superior antibacterial activity, stability and corneal permeability. However, it is known to cause fusion, desquamation and morphological change of corneal epithelial cells and induce various inflammatory lesions such as contact dermatitis, conjunctivitis, rhinitis, etc. when used for a long time. For human, long-term use of BAC can lead to severe damage of corneal endothelial cells because they have limited regenerative ability. In particular, use of BAC-containing eye drops may cause severe keratitis when there are insufficient corneal epithelial cells or their function is decreased. In this test example, cornea damage was induced in experimental animals using BAC.

6-week-old, male BALB/c albino mice weighing 18-20 g were used as experimental animals, 6 per group. The experimental animals were accustomed to the laboratory environment for 7 days (25±1° C., 40±5% humidity). For an animal model of cornea damage, cornea damage was induced by dropping 0.2% benzalkonium chloride (BAC, 5 µL) in the eyes 2 times (9 am and 9 pm) a day for 14 days. For a normal control group, PBS was dropped in the eyes. From day 3, the extract obtained in Example was orally administered every day at a dosage of 50 or 10 mg/kg, avoiding the time when BAC or PBS was dropped in the eyes.

TEST EXAMPLE 2

Corneal Fluorescein Staining

Figure 1A:
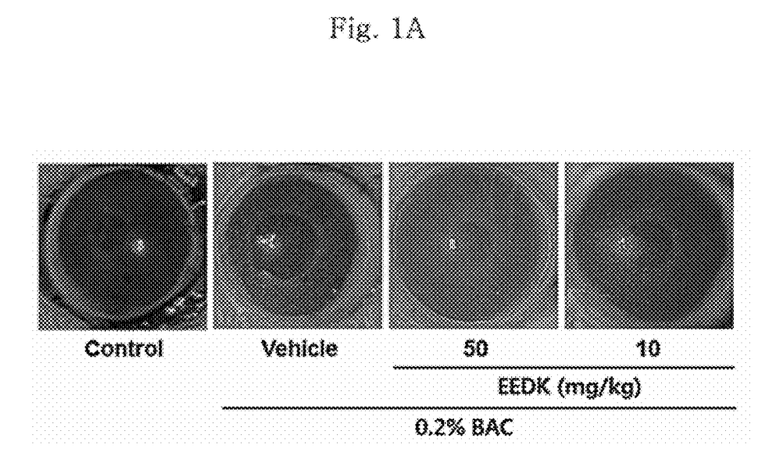
FIGS. 1a and 1b show a result of investigating the protective effect of an extract of a persimmon tree against cornea damage in an animal model of BAC-induced cornea damage by fluorescent staining.
Figure 1B:
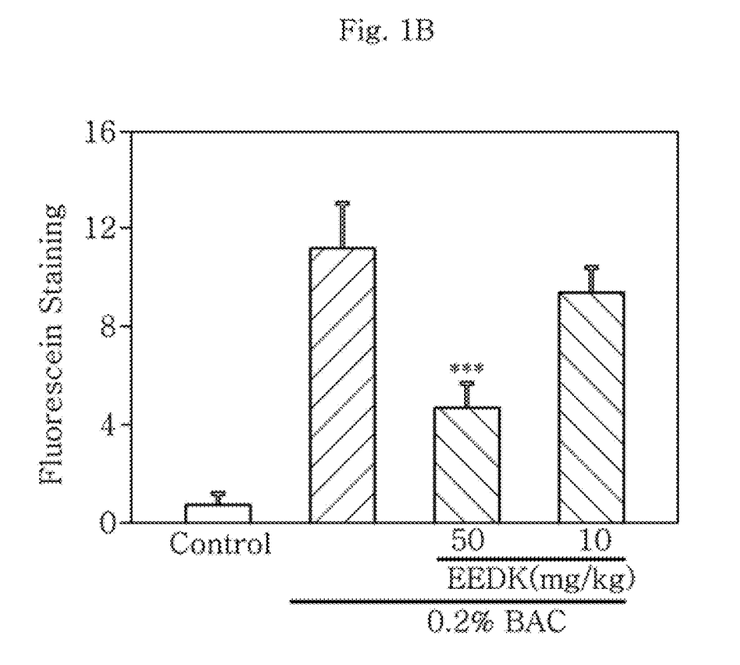

After anesthetizing the experimental animals, the damage to the cornea was observed using a fluorescent dye (sodium fluorescein). Specifically, after dropping 1 µL of 0.1% sodium fluorescein onto the eyes of the experimental animals, the damage of corneal cells was observed using a slit lamp (see FIGS. 1a and 1b).

TEST EXAMPLE 3

Western Blot Analysis

Figure 2:
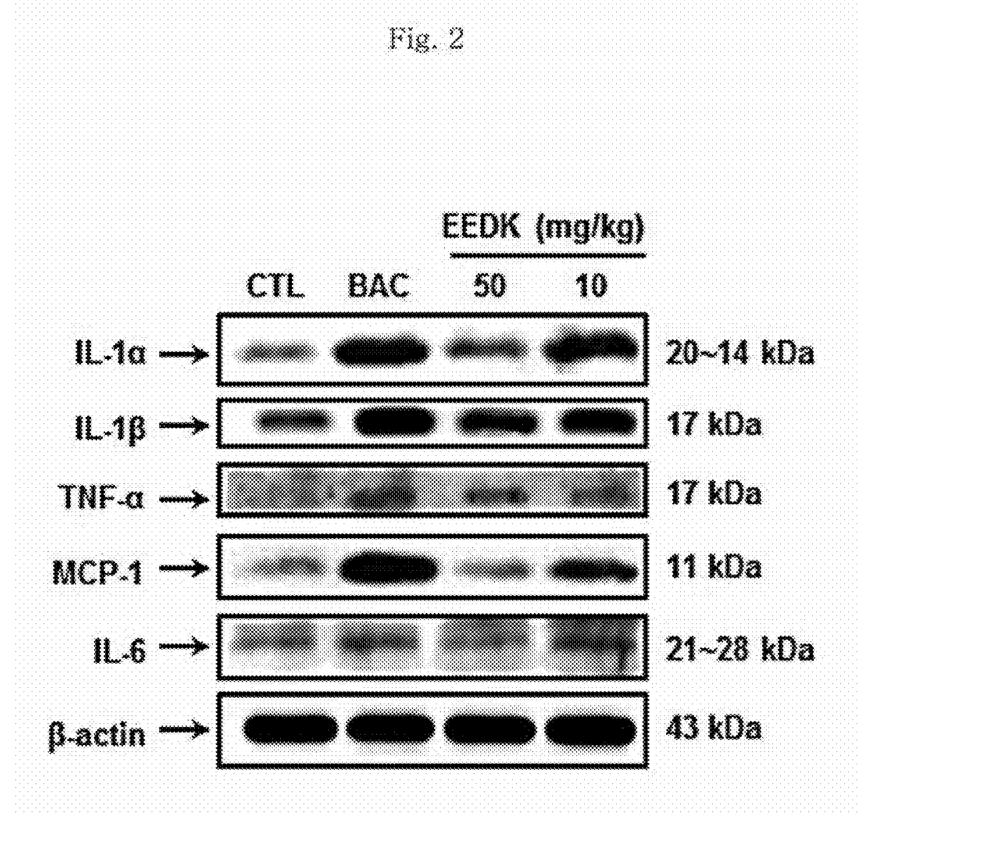
FIG. 2 shows a result of investigating the effect of an extract of a persimmon tree on the expression of inflammatory cytokines in an animal model of BAC-induced cornea damage.

Proteins extracted from the corneal tissue were subjected to SDS-PAGE. After incubating overnight at 4° C. with cytokine primary antibodies, the membrane was washed and incubated at room temperature for 2 hours with secondary antibodies. The expression level of proteins was measured using the Las-4000 image reader and the Multi Gauge 3.1 software (Fuji Photo Film, Japan) (see FIG. 2).

TEST EXAMPLE 4

Hematoxylin & Eosin Staining

Figure 3:
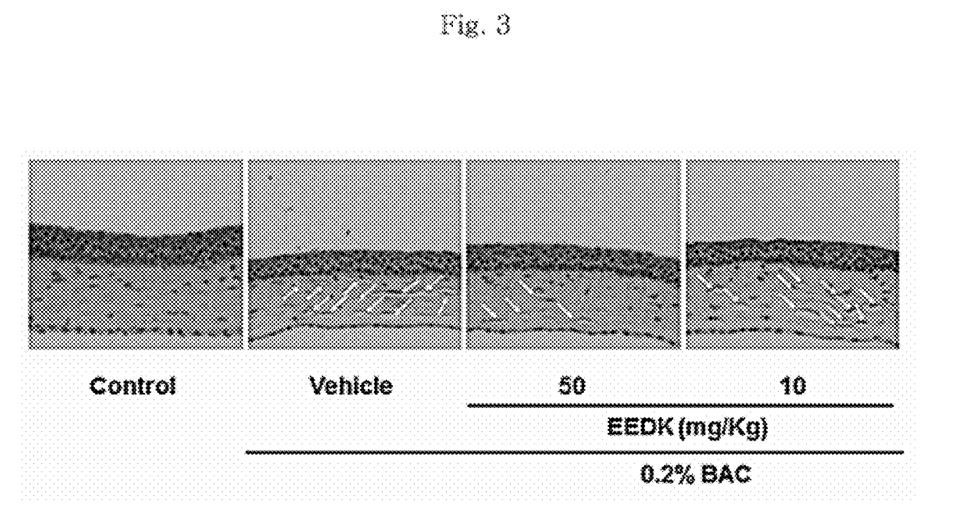
FIG. 3 shows a result of investigating the protective effect of an extract of a persimmon tree against the damage of the corneal stroma in animal model of BAC-induced cornea damage by hematoxylin and eosin staining.

The corneal tissue was sectioned, fixed in 4% paraformaldehyde (pH 7.4) for 20 minutes and then washed with PBS. Subsequently, after fixing the tissue on a slide using acetic acid, the nucleus was stained with hematoxylin and the cytosol was stained with eosin. The change in the thickness of the cornea and the condition of the corneal stroma was observed using an optical microscope (see FIG. 3).

TEST EXAMPLE 5

Immunohistochemistry

Figure 4:
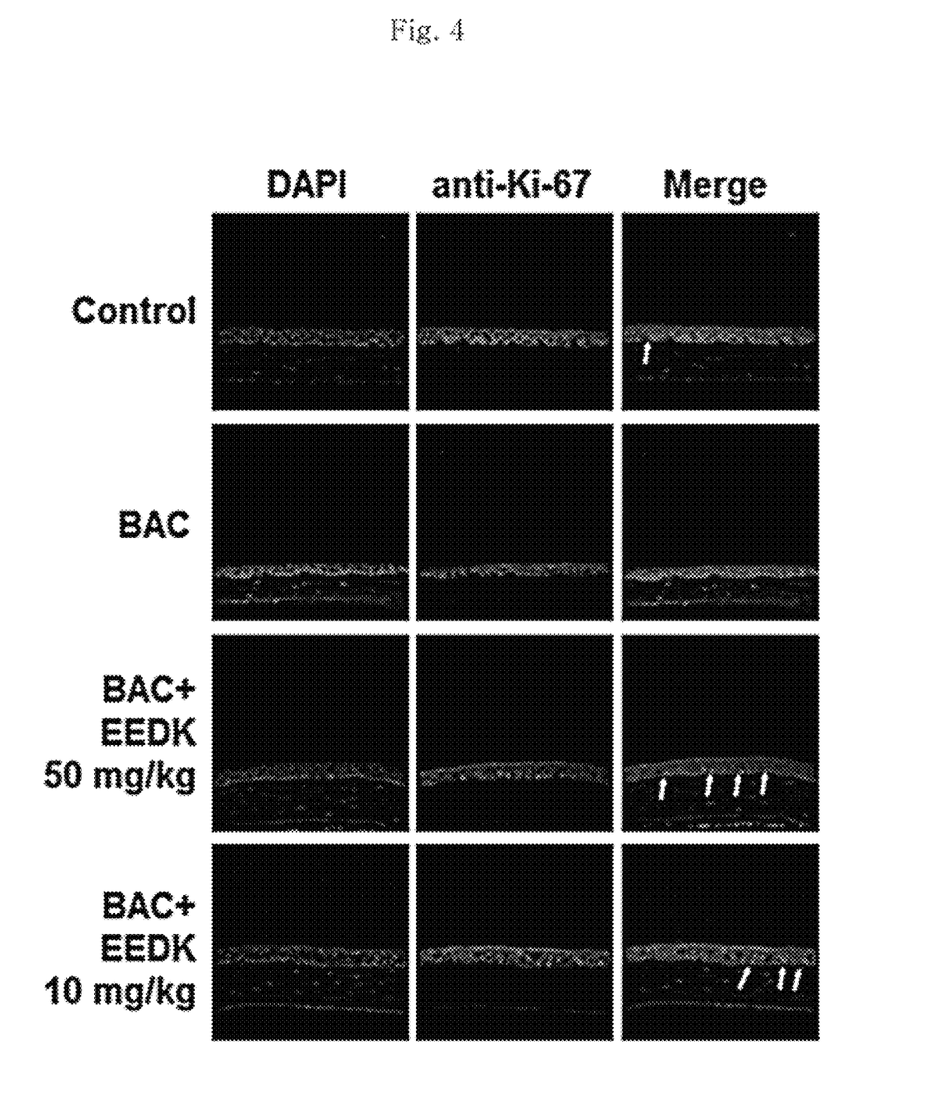
FIG. 4 shows a result of investigating the effect of an extract of a persimmon tree on the expression of corneal proliferative proteins in an animal model of BAC-induced cornea damage by immunohistochemical staining.

After being deparaffinized and rehydrated, the corneal section was incubated with anti-Ki67 capable of marking cellular proliferation. Immunohistochemical staining was performed by attaching primary antibodies and then attaching anti-Alexa 594 antibodies. The nucleus was stained with a DAPI mounting solution. Then, the cornea was observed using a confocal microscope (see FIG. 4).

EXPERIMENTAL RESULTS (1) From the result of investigating the protective effect of the extract of a persimmon tree against cornea damage in the animal model of BAC-induced cornea damage by fluorescent staining (see FIGS. 1a and 1b), it can be seen that the cornea damage-induced group shows more cornea damage than the normal group and that the administration of the extract of a persimmon tree to the cornea damage-induced group reduces cornea damage. Accordingly, it can be seen that the extract of a persimmon tree according to the present disclosure protects the cornea and inhibits cornea damage by inhibiting the damage to corneal cells and corneal layers.

(2) From the result of investigating the effect of the extract of a persimmon tree on the expression of inflammatory cytokines in the animal model of BAC-induced cornea damage by western blotting (see FIG. 2), it can be seen that the expression of the inflammatory cytokines IL-1α, IL-1β, TNF-α, MCP-1 (monocyte chemoattractant protein-1) and IL-6 is increased in the cornea damage-induced group. It can also be seen that the administration of the extract of a persimmon tree to the cornea damage-induced group inhibits the expression of the inflammatory cytokines IL-1α, IL-1β, TNF-α, MCP-1 (monocyte chemoattractant protein-1) and IL-6 activated by cornea damage. Accordingly, it can be seen that the extract of a persimmon tree according to the present disclosure is effective in suppressing inflammatory responses of corneal cells and protecting the corneal cells.

(3) From the result of investigating the protective effect of the extract of a persimmon tree against damage to the corneal stromal layer in the animal model of BAC-induced cornea damage by hematoxylin and eosin staining (see FIG. 3), it can be seen that the cornea damage-induced group shows decreased thickness of the corneal stromal layer. It can also be seen that this phenomenon is suppressed in the group to which the extract of a persimmon tree has been administered. Accordingly, it can be seen that the extract of a persimmon tree according to the present disclosure inhibits damage to the corneal stromal layer induced by BAC and protects corneal cells.

(4) From the result of investigating the effect of the extract of a persimmon tree on the expression of corneal proliferative proteins in the animal model of BAC-induced cornea damage by immunohistochemical staining (see FIG. 4), it can be seen that the expression of the Ki-67 protein, which is a marker for proliferation of proliferative cells in the corneal epithelial layer, is increased in the group to which the extract of a persimmon tree has been administered. Because the increased expression of the corneal proliferative proteins occurs during the healing of the cornea by the corneal epithelial cells, it can be seen that the extract of a persimmon tree according to the present disclosure helps the proliferation of new corneal epithelial cells, thereby inhibiting cornea damage and protecting the cornea, by increasing the expression of the corneal proliferative proteins.

Hereinafter, the present disclosure will be described in detail through formulation examples. However, the following formulation examples are for illustrative purposes only and the scope of the present disclosure is not limited by them.

FORMULATION EXAMPLE 1

Soft Capsule

A soft capsule was prepared by mixing 150 mg of a persimmon leaf extract with 2 mg of palm oil, 8 mg of hydrogenated palm oil, 4 mg of yellow beeswax and 6 mg of lecithin and filling 400 mg of the mixture per capsule according to a common method.

FORMULATION EXAMPLE 2

Tablet

After forming a granule by mixing 150 mg of a persimmon leaf extract with 100 mg of glucose, 50 mg of a red ginseng extract, 96 mg of starch and 4 mg of magnesium stearate and adding 40 mg of 30% ethanol, the granule was dried at 60° C. and prepared into a tablet using a tablet-making machine.

FORMULATION EXAMPLE 3

Granule

After forming a granule by mixing 150 mg of a persimmon leaf extract with 100 mg of glucose, 50 mg of a red ginseng extract and 600 mg of starch and adding 100 mg of 30% ethanol, the granule was dried at 60° C. and filled in a pouch. The final weight was 1 g.

FORMULATION EXAMPLE 4

Drink 150 mg of a persimmon leaf extract was mixed with 10 g of glucose, 50 mg of a red ginseng extract, 2 g of citric acid and 187.8 g of purified water and filled in a bottle. The final volume was 200 mL.

| [Formulation Example 5] Health food | |
|---|---|
| Persimmon leaf extract | 1000 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

Although the above-described compositions of the vitamin and mineral mixtures are given as specific examples relatively appropriate for health food, the compositions may be changed as desired. After preparing a granule by mixing the above ingredients according to a common health food preparation method, a health food was prepared according to a common method.

| [Formulation Example 6] Health drink | |
|---|---|
| Persimmon leaf extract | 1000 mg |
| Citric acid | 1000 mg |
| Oligosaccharide | 100 g |
| Plum concentrate | 2 g |
| Taurine | 1 g |
| Purified water | to make 900 mL |

According to a common health drink preparation method, the above ingredients were mixed and heated for about 1 hour at 85° C. under stirring. The resulting solution was filtered, filled in a sterilized 2-L bottle, sealed, sterilized and then kept in a refrigerator.

Although the above-described compositions of the vitamin and mineral mixtures are given as specific examples relatively appropriate for drink, they may be varied as desired in consideration of particular consumers, country, purpose of use, regional or ethnic preference, etc.

Those of ordinary skill in the art to which the present disclosure belongs will be able to make various changes and modifications within the scope of the present disclosure.

While the specific exemplary embodiments have been shown and described, it will be obvious to those skilled of ordinary skill in the art that they are provided only as specific examples and the scope of the present disclosure is not limited by them. It is to be understood that the scope of the present disclosure is defined by the appended claims and their equivalents.

What is claimed is:

1. A method for improving or treating cornea damage in a subject in need thereof comprising administering to said subject a composition comprising an effective amount of an extract from the leaves of a persimmon tree.

2. The method for improving or treating cornea damage according to claim 1, wherein the extract is administered in the form of a pharmaceutical composition.

3. The method for improving or treating cornea damage according to claim 1, wherein the extract is administered in the form of a health food composition.

4. The method for improving or treating cornea damage according to claim 1, wherein the persimmon tree is *Diospyros kaki*.

5. The method for improving or treating cornea damage according to claim 1, wherein the extract is a $C_1$-$C_6$ alcohol extract.

6. The method for improving or treating cornea damage according to claim 1, wherein the cornea damage is caused by a corneal disease or causes a corneal disease.

7. The method for improving or treating cornea damage according to claim 1, wherein the cornea damage is one or more selected from a group consisting of keratitis, corneal ulcer and corneal abrasion.

8. The method for improving or treating cornea damage according to claim 1, wherein the extract inhibits the expression of inflammatory cytokines.

9. The method for improving or treating cornea damage according to claim 8, wherein the inflammatory cytokine is one or more selected from a group a group consisting of IL-1α, IL-1β, TNF-α, MCP-1 (monocyte chemoattractant protein-1) and IL-6.

10. The method for improving or treating cornea damage according to claim 1, wherein the extract inhibits the damage of the corneal stromal layer.

11. The method for improving or treating cornea damage according to claim 1, wherein the extract promotes the proliferation of corneal epithelial cells.

12. The method for improving or treating cornea damage according to claim 2, wherein the pharmaceutical composition contains 0.1-50 wt % of the extract.

13. The method for improving or treating cornea damage according to claim 2, wherein the pharmaceutical composition contains 1.0-10 wt % of the extract.

14. The method of claim 1, wherein the effective amount is 0.001-100 mg/kg of the extract, wherein the extract is administered at least once per day, and wherein the extract is a freeze-dried extract.

* * * * *